(12) United States Patent
Soubeiran (10) Patent No.: US 9,579,203 B2
(45) Date of Patent: Feb. 28, 2017

(54) DEVICE FOR THE DISPLACEMENT OF TISSUES, ESPECIALLY BONE TISSUES

(76) Inventor: Arnaud Soubeiran, Paris (FR)

( * ) Notice: Subject to any disclaimer, the term of this patent is extended or adjusted under 35 U.S.C. 154(b) by 537 days.

(21) Appl. No.: 13/069,903

(22) Filed: Mar. 23, 2011

(65) Prior Publication Data

US 2011/0238126 A1    Sep. 29, 2011

(30) Foreign Application Priority Data

Mar. 23, 2010  (FR) ...................... 10 01127

(51) Int. Cl.
| | | |
|---|---|---|
| *A61B 17/72* | (2006.01) | |
| *A61F 2/28* | (2006.01) | |
| *A61F 2/38* | (2006.01) | |
| *A61F 2/36* | (2006.01) | |
| *A61F 2/30* | (2006.01) | |
| *A61F 2/48* | (2006.01) | |

(52) U.S. Cl.
CPC ............. *A61F 2/28* (2013.01); *A61B 17/7216* (2013.01); *A61F 2/3804* (2013.01); *A61F 2/384* (2013.01); *A61F 2/3607* (2013.01); *A61F 2002/2825* (2013.01); *A61F 2002/3055* (2013.01); *A61F 2002/30079* (2013.01); *A61F 2002/30523* (2013.01); *A61F 2002/30601* (2013.01); *A61F 2002/30668* (2013.01); *A61F 2002/30706* (2013.01); *A61F 2002/48* (2013.01)

(58) Field of Classification Search
USPC ......... 606/53–60, 62–63, 86 R, 90, 105, 258
See application file for complete search history.

(56) References Cited

U.S. PATENT DOCUMENTS

| | | | |
|---|---|---|---|
| 6,849,076 B2 | 2/2005 | Blunn et al. | |
| 8,043,299 B2 * | 10/2011 | Conway | .................. 606/105 |
| 8,137,349 B2 * | 3/2012 | Soubeiran | ................. 606/63 |
| 8,419,801 B2 * | 4/2013 | DiSilvestro et al. | ...... 623/23.47 |
| 8,439,915 B2 * | 5/2013 | Harrison et al. | ............... 606/60 |
| 2004/0193266 A1 * | 9/2004 | Meyer | ................. 623/16.11 |
| 2005/0010233 A1 * | 1/2005 | Wittenstein | ........ A61B 17/7216 |
| | | | 606/90 |
| 2005/0246034 A1 | 11/2005 | Soubeiran | |
| 2006/0004459 A1 * | 1/2006 | Hazebrouck et al. | ..... 623/18.12 |
| 2006/0069447 A1 * | 3/2006 | DiSilvestro et al. | ...... 623/23.16 |
| 2007/0270803 A1 | 11/2007 | Giger et al. | |
| 2009/0254088 A1 * | 10/2009 | Soubeiran | ..................... 606/63 |

(Continued)

FOREIGN PATENT DOCUMENTS

| | | |
|---|---|---|
| FR | 2901991 A1 | 12/2007 |
| FR | 2949662 A1 | 3/2011 |

(Continued)

*Primary Examiner* — Matthew Lawson
(74) *Attorney, Agent, or Firm* — Scott E. Kamholz; Foley Hoag LLP (57) ABSTRACT

Device for displacing tissues inside the organism, e.g. bone tissues, comprising an index part (1), a transport part (2), a threaded rod, a nut (4) mounted on the threaded rod, a drive shaft and a drive connector (71, 72, 73) linking the drive shaft to the nut (4), the transport part (2) being slidably mounted with respect to the index part (1) and limited in rotation with respect to the index part (1) by a first stop (34) which cooperates with a first bracket (14, 15) of the index part, wherein the rotation of the threaded rod with respect to the index part (1) is blocked by the first stop (34), the nut (4) being free to rotate (34) with respect to the index part (1).

14 Claims, 5 Drawing Sheets

(56) References Cited

U.S. PATENT DOCUMENTS

2010/0049204 A1    2/2010   Soubeiran
2010/0217271 A1*   8/2010   Pool et al. ..................... 606/90
2010/0280519 A1   11/2010   Soubeiran

FOREIGN PATENT DOCUMENTS

| WO | 01178614 A1 | 10/2001 |
| WO | 2007144489 A2 | 12/2007 |
| WO | 2009058546 A1 | 5/2009 |

\* cited by examiner

DEVICE FOR THE DISPLACEMENT OF TISSUES, ESPECIALLY BONE TISSUES

The present disclosure relates to devices for displacing tissues inside an organism, e.g. bone tissues, the geometry of which may be modified progressively and reversibly without re-operation or anesthesia, and more specifically those using a threaded rod mounted in such a way that it works only in tension and its loaded length decreases as the device expands.

BACKGROUND

Earlier devices for displacing tissues inside an organism, e.g. bone tissues, the geometry of which may be modified progressively and reversibly without re-operation nor anesthesia, use a threaded rod which works in compression and the loaded length of which increases as the device elongates, with an increasing buckling risk and with the necessity, in order to obtain sufficient stress to rotate the screw, to use a reducer system, which is space eating and expensive, such as those disclosed in documents U.S. Pat. No. 6,849,076, US20070270803 or WO2009058546.

SUMMARY

The inventor has developed new devices which maintain the advantages of known designs in which the threaded rod is mounted in such a way that it works only in tension and that its loaded length decreases as the device elongates, and at the same time allow for a greater growth potential for a given length of the device, and has an enhanced mechanical resistance to flexion.

The presently disclosed devices for tissue displacement within the organism, e.g. bone tissues, include an index part, a transport part, a threaded rod, a nut mounted onto the threaded rod, a drive shaft and a drive connector that links the drive shaft to the nut, the transport part being slidably mounted with respect to the index part and limited in rotation with respect to the index part by a first stop which cooperates with a first bracket of the index part, the rotation of the threaded rod with respect to the index part being prevented by the first stop, the nut being free to rotate with respect to the index part.

Such an arrangement allows friction to be confined to the nut only (friction being present at two sites, the nut and the stop/bracket contact, in prior devices) thereby allowing for a more fluid operation of the device: in the known designs, the nut may rotate without movement of the stop/bracket contact and vice-versa, the screw being subject to a torsion between both friction sites, which induces a hysteresis between the rotating angle of the drive shaft and the effective expansion of the device, together with a surge operation. In the presently disclosed devices, the nut rotates if all friction has been overcome and provokes a direct variation of length of the device.

Advantageously, the first stop is fixed to an end of the threaded rod, the first bracket being fixed to an end of the index part, the first stop and the nut being located on both sides of the first bracket, longitudinal translation of the threaded rod with respect to the index part in the direction of the first stop towards the first bracket being limited by the cooperation of the first stop with the first bracket.

Advantageously, the device may include a second stop fixed to one end of the threaded rod and capable of cooperating with a second bracket fixed to the index part for limiting the longitudinal translation of the threaded rod with respect to the index part in the direction of the first bracket towards the first stop, said first bracket and second bracket being capable of displacing along the threaded rod between said first bracket and second bracket.

Indeed, in a presently disclosed device for displacing tissues inside the organism, especially bone tissues, which includes an index part with a first and second end, a transport part with a first and second end and slidably mounted with respect to the index part, a threaded rod with a first and second end, the first and second ends of the transport part and of the threaded rod being constantly on the side of the first end of the index part with respect to its second end, a first stop fixed to the second end of the threaded rod and which cooperates with a first bracket fixed to the second end of the index part for limiting the longitudinal translation of the threaded rod with respect to the index part in the direction of the first stop towards the first bracket, a nut mounted onto the threaded rod, the first stop and the nut being disposed on both sides of the first stop, converter for transforming the displacement in a first direction of the nut along the threaded rod into displacement of the transport part with respect to the index part and a drive shaft:

the first stop cooperates also with the first bracket in order to prevent rotation of the threaded rod with respect to the index part, the nut is free to rotate with respect to the index part, and drive connector links the drive shaft to the nut.

Advantageously, a device may also include:

a second bracket fixed to the first end of the threaded rod and capable of cooperating with a second bracket fixed to the index part for limiting the longitudinal translation of the threaded rod with respect to the index part in the direction of the first bracket towards the first stop, said first and second brackets being located between said first and second stops and said nut being capable of displacing along the threaded rod between said first and second brackets.

a converter for transforming the displacement in the second direction, opposite the first direction, of the nut along the threaded rod into displacement of the transport part with respect to the index part.

According to various embodiments:

The drive shaft may include a permanent magnet.

The permanent magnet may be a neodymium having a substantially diametral magnetization direction, said magnet including an axial hole e.g. for allowing passage of the threaded bore and the drive connector which links the drive shaft to the nut is a rigid envelope fixed to the nut and in which the permanent magnet is maintained.

The converter for transforming the displacement in a first direction of the nut along the threaded rod into a displacement of the transport part with respect to the index part may include a first bracket surface fixed to the nut and a second bracket surface fixed to the transport part, capable of cooperating and substantially perpendicular to the axis of the threaded rod.

The converter for transforming the displacement in a second direction of the nut along the threaded rod into displacement of the transport part with respect to the index part may include a third bracket surface fixed to the nut and a fourth bracket surface fixed to the transport part, capable of cooperating and substantially perpendicular to the axis of the threaded rod.

The first bracket may cooperate with surfaces of the transport part for guiding in rotation and limiting the translation of the latter with respect to the index part.

BRIEF DESCRIPTION OF THE DRAWINGS

Structure and advantages of the presently disclosed devices for displacement of tissues inside the organism, especially bone tissues, shall be better understood in the course of the following description of various embodiments, made with reference e.g. to the appended drawings in which.

Figure 4:
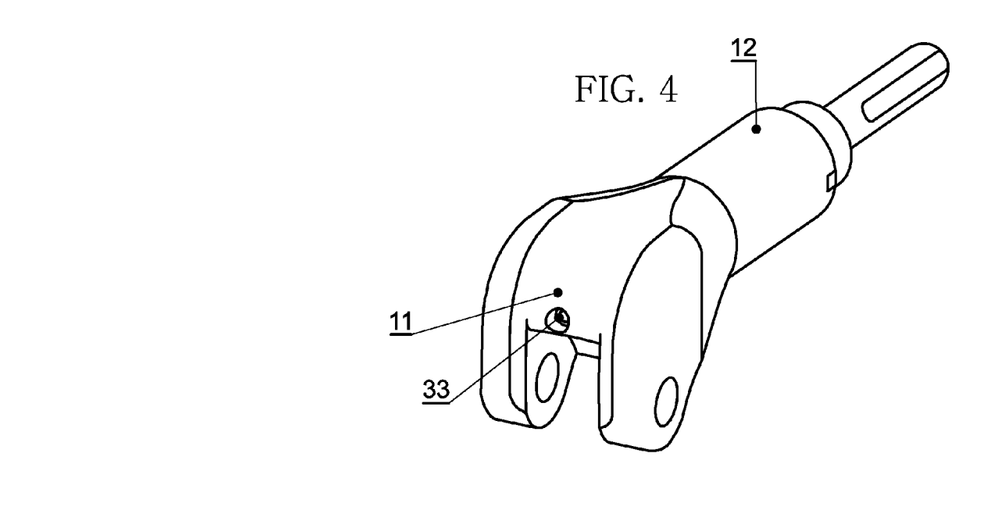
FIG. 4 is a perspective view of a device according to a second embodiment.
Figure 5:
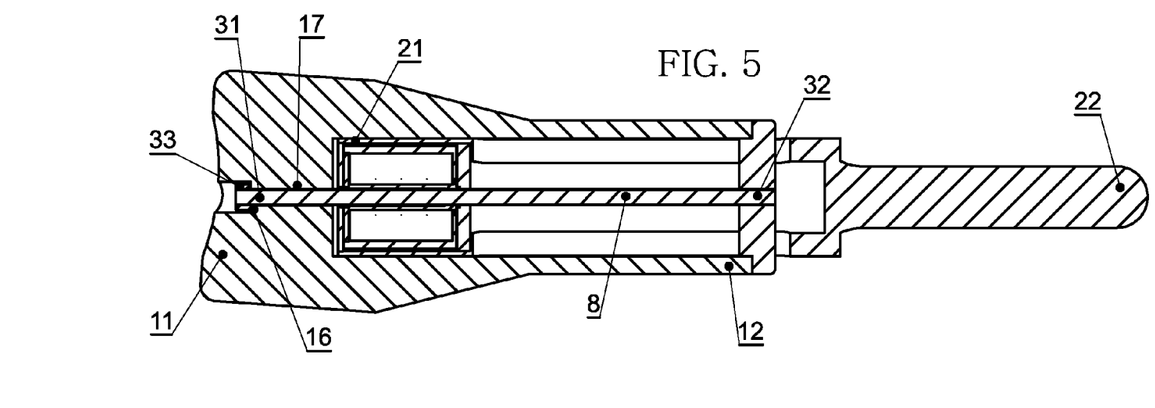
FIG. 5 is a cut view of the device of FIG. 4, assembled and before expansion.

It shall be noted that if a numeral reference may not be found on a figure it might easily be found on another. In particular, for a better reading, the parts already referenced on FIGS. 1-3 and re-used in FIGS. 4 and 5 are not all referenced thereon.

DETAILED DESCRIPTION

Figure 1:
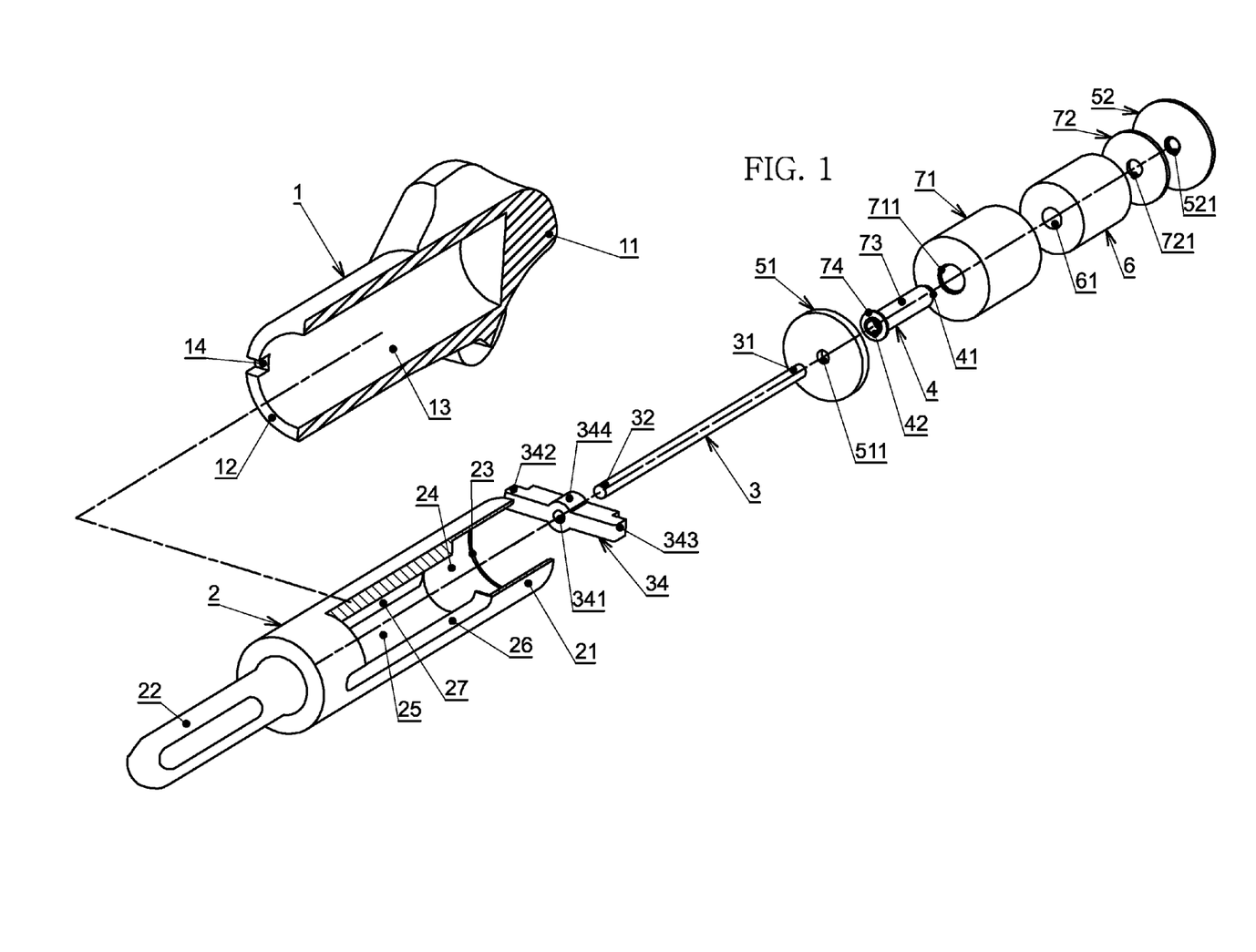
FIG. 1 is an exploded perspective view in which two parts are partly cutaway, of a device according to a first embodiment.
Figure 2:
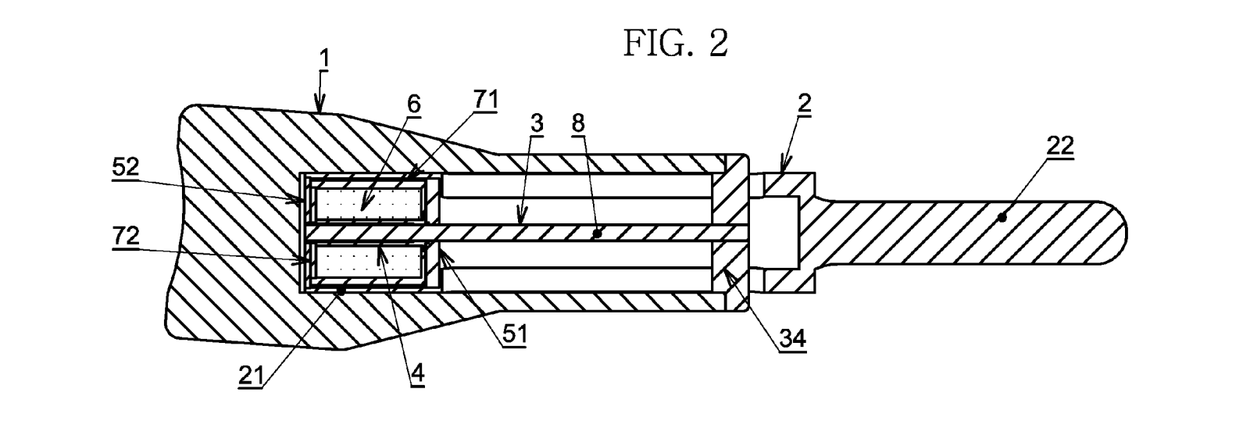
FIG. 2 is a cut view of the device of FIG. 1, assembled and before expansion.
Figure 3:
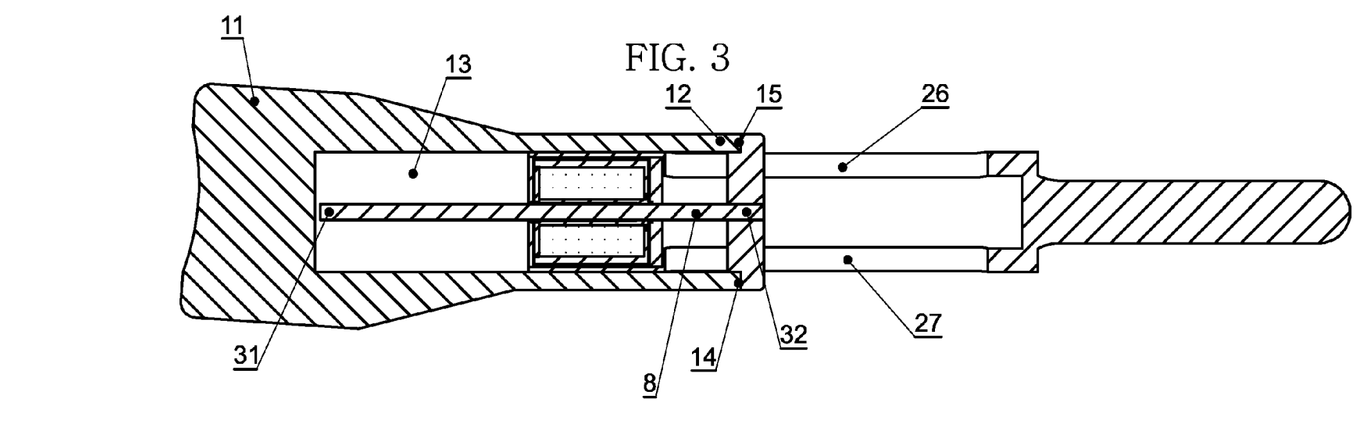
FIG. 3 is a cut view of the device of FIG. 1, assembled and after a partial expansion.

Reference is now made to FIGS. 1-3 which represent a first embodiment well adapted to the manufacture of expandable prostheses. For this non limiting example of the first embodiment, a distal femur expandable prosthesis is shown and disclosed. It includes:

an index part 1 with
   a first distal end 11, in the known outer shape of a hinged prosthetic distal femur, capable of cooperating with an axis and a tibial part (not represented), and a second proximal end 12 substantially cylindrical and provided with a cylindrical housing 13 substantially along the axis corresponding to that of the replaced bone part. The second end 12 also carries two recesses 14, 15 a face of which is perpendicular and two faces are substantially parallel to the axis of the cylindrical housing 13;

a transport part 2 with a first cylindrical end 21 dimensioned in such a way to be capable of sliding within the cylindrical housing 13 of the index part 1 and which includes, along its axis:
   two first and second counterbores 23, 24 and a successive bore 25, of decreasing diameters and which open on the side of the first end 21 and
   two longitudinal elongated throats 26, 27 positioned in such a way that the recesses 14, 15 of the index part 1 always face each other when the transport part 2 is assembled, regardless of the expansion state of the prosthetic femur. The second end 22 of the transport part 2 is tail-shaped and may be cemented or press-fitted within the medullary cavity of the residual part of the bone to be rebuild;

a threaded rod 3 with a first end 31 and a second end 32;

an arm 34, so-called first stop having a substantially rectangular section, the ends 342, 343 of which are capable of cooperating with both recesses 14, 15 respectively, at the second end 12 of the index part 1, such recesses 14, 15 forming the first bracket. The arm 34 also includes substantially in its center a thread 341 capable of receiving the second end 32 of the threaded rod 3, and may include a stiffening protrusion 344 around the thread or have a constant thickness in the direction perpendicular to the threaded rod 3, sufficient for providing resistance to the applied load;

a nut 4 the inside thread of which is capable of cooperating with the threaded rod, the outside 73 of which is preferably cylindrical but may also be e.g. hexagonal, and which includes a first end face 41 and a second end face 42 together with a first shoulder 74 close to the second end 42;

a first bearing washer 51 having in its center a hole 511 the diameter of which is slightly greater than that of the threaded rod 3 and which, at the periphery of one of its faces, leans onto the bottom of the second counterbore 24 of the transport part 2 and cooperates, at the periphery of its hole 511 on its opposite face, with the second end face 42 of the nut 4, thereby together forming the converter 42, 51 for transforming the displacement in a first direction of the nut 4 along the threaded rod 3 into a displacement of the transport part 2 with respect to the index part 1;

a neodymium (i.e. neodymium, iron, boron) magnet 6 resistant to the sterilization temperature, substantially cylindrical and having along its axis a hole 61 in which may be introduced and maintained the nut 4, i.e. by gluing by way of a silicone glue, such magnet 6 forming the drive shaft;

a cover 71 in the shape of a tube segment, closed at an end by a planar wall, except an opening 711 which fits over the shoulder 74 of the nut 4, the cover 71 being closed, at the opposite end, by a washer 72 which outer perimeter matches the open end of the cover 71, the central opening 711 just leaving a passage for the end 41 of the nut 4, the cover 71 and the washer 72 forming, together with the outer face 73 of the nut 4, a cavity which insulates the magnet 6 from the biological environment, the cover 71 and the washer 72 forming, with the glue that maintains the magnet 6 within this cavity, the drive connector 71, 72 which links the drive shaft 6 to the nut, the glue being preferably a silicone glue well tolerated by the organism. The outer face 73 of the nut 4 and the central hole 61 of the magnet may also have a section that prevents them from rotating with respect to each other, such as a hexagonal section;

A second bearing washer 52 having in its center a hole 521 the diameter of which is slightly greater than that of the threaded rod 3 and which, at the periphery of one of its faces, bears on the bottom of the first counterbore 23 of the transport part 2 and cooperates, at the periphery of its hole 521 on the same face, with the first end face 41 of the nut 4, thereby together forming the converter 52, 41 for transforming the displacement in the second direction opposite to the first direction of the nut 4 along the threaded rod 3 into a displacement of the transport part 2 with respect to the index part 1. This second bearing washer 52 may be omitted if only operation in the expansion direction is required.

The first counterbore 23 of the transport part 2 is dimensioned to receive without clearance the second bearing washer 52.

The second counterbore 24 of the transport part 2 is dimensioned to receive in addition the first bearing washer 51, the magnet 6 and its cavity 71, 72, 73 with a clearance sufficient to permit rotation of the latter assembly.

The bore 25 of the transport part 2 is dimensioned such that the first stop 34, if it includes a stiffening protrusion 344, may be inserted therein, with its greater length along the axis of the bore 25, and then rotated in its operating position across the longitudinal elongated throats 26, 27 of the transport part 2, the thickness of the first stop 34 being slightly smaller that the width of the throats 26, 27 so as to be capable of sliding therein, except the protrusion 244. In an alternate embodiment, the stiffening protrusion 344 is absent and the arm 34 forming the first stop has a constant thickness sufficient for resisting to predicted loads, the bore 25, which is then no longer in use, is omitted and the throats 26, 27 merged in one sole throat having a width slightly greater than the thickness of the arm 34 and which is also sufficient to allow for passage of the threaded rod 3 after the arm 34 has been introduced by one side opening to said sole throat.

The distal femur according to the first embodiment is assembled in the following manner:
- the nut 4 and the cover 71 are assembled and welded together at the junction between the shoulder 74 of the nut 4 and the corresponding opening 711 of the cover. The housing thus created is glued e.g. by way of a silicone glue well tolerated by the organism and the magnet 6 is introduced therein with pressure, so as to spread the glue all around. The washer 72 is assembled and welded at its periphery to the cover 71, thereby closing the cavity of the magnet 6.
- the first stop 34 is introduced within the bore 25 of the transport part 2 and rotated across the elongated longitudinal throats 26, 27 in such a way to put the stop 34 its normal operation position, its faces 14, 15 capable of cooperating with the first bracket being turned towards the bored first end 21 of the transport part 2;
- the threaded rod 3 is screwed in the thread 341 of the first stop 34 and laser welded at an end onto the first stop 34, across one of the longitudinal elongated throats 26, 27;
- the bearing washer 51 is inserted until its stops against the planar bottom of the second counterbore 24, and the nut 4 is then screwed on the threaded rod 3 and, finally the bearing washer 52 takes its place within the first counterbore 23, of greater diameter, and is welded at its periphery;

The resulting assembly is then inserted into the cylindrical housing 13 of the index part 1 to form the expandable distal femur prosthesis according to the first embodiment.

The distal femur prosthesis according to the first embodiment may be expanded in the following manner:
- the drive shaft 6 is rotated in the expansion direction, which is that in which the nut 4 moves along the threaded rod 3 towards the first stop 34 and which depends upon the pitch of the threaded rod 3, by operation of a rotating magnetic field created by an external field source
  - which is advantageously a permanent magnet hand-operated and which one rotates around the leg maintaining one of its poles, i.e. the north pole, constantly turned towards the magnet 6
  - or, whenever it is not possible to turn 360° at a reasonable distance at the height of the magnet, such as the height of the ankle for example, which is alternately half-turned around the leg with the north pole facing the magnet 6, then half-turned again around the leg with the south pole facing the magnet 6, both half-turns being initiated and achieved at the same places. The pitch of the threaded rod 3 is, for example, between 0.1 and 0.2 mm, so that five to ten revolutions or ten to twenty half-turns will induce a 1 mm expansion. Several known electromagnetic, or mechanical or electromechanical devices capable of driving a permanent magnet, may also create such a rotating field.

Rotation of the drive shaft 6 drives rotation of the nut 4 via the drive connector 71, 72, 73 that links the drive shaft 6 to the nut 4 and the translation of the nut 4 towards the first stop 34 along the threaded rod 3. The threaded rod 3 is supported on the index part 1 via the first stop 34 and the first bracket 14, 15, the nut 4 translates as well with respect to the index part 1, and the transport part 2 is moved away from the index part 1 by the converter 51, 42 for transforming the displacement in a first direction of the nut 4 along the threaded rod 3 into a displacement of the transport part 2 with respect to the index part 1.

Rotation of the drive shaft 6 in a first direction thus drives the expansion of the femur prosthesis according to the first embodiment, rotation of the drive shaft 6 in the opposite direction drives the shortening thereof but only when external forces are applied, such as tension of soft tissues and the patient's weight, capable of moving the first stop 34 against the first bracket 14, 15.

Thus, in the first embodiment:
- the first ends 21, 31 of the transport part 2 and of the threaded rod 3 are constantly on the side of the first end 11 of the index part with respect to its second end 12, whichever the phase of expansion of the device;
- the first stop 34 and the nut 4 are located on both sides of the first bracket 14, 15,
- the first stop 34 which cooperates with the recesses 14, 15 via their faces perpendicular to the axis of the cylindrical housing 13, in order to limit the longitudinal translation of the threaded rod 3 with respect to the index part, also cooperates with the recesses 14, 15, via their faces substantially parallel to the axis of the cylindrical housing, in order to prevent rotation of the threaded rod 3 with respect to the index part 1;
- the nut 4 is free to rotate with respect to the index part 1;
- The first stop 34 also cooperates with the longitudinal elongated throats 26, 27 of the transport part 2 in order to guide in rotation and to limit translation the transport part 2 with respect to the index part 1.

Reference is now made to FIGS. 4 and 5 which disclose a second embodiment well adapted to use as expandable prostheses, but also as bone lengthening nails, bone transport nails, and thorax and spinal distraction rods. For this non-limiting example of the second embodiment, a distal femur expandable prosthesis again is represented. It is similar to that of the first embodiment, except that the threaded rod 3 extends on the side of its first end 31 through a hole 17 within the index part 1, opening at the first end 11 thereof within a counterbore the bottom of which forms a second bracket 16 capable of receiving a second stop 33 fixed, e.g. by screwing and welding, to the first end 31 of the threaded rod 3 in order to prevent its longitudinal translation with respect to the index part 1, this time in the direction of the first bracket 14, 15 towards the first stop 34.

FIG. 4 shows a perspective view of the distal femur expandable prosthesis according to the second embodiment, in which the position of the second stop 33 is visible.

FIG. 5 shows a cut of this prosthesis before expansion.

Mounting this expandable distal femur prosthesis according to the second embodiment begins like that of the first embodiment but, once the transport part 2 has been introduced within the cylindrical housing 13 of the index part 1, it continues and ends with the screwing and the welding at an end of the second stop 33 onto the first end 31 of the threaded rod 3.

The expandable distal femur prosthesis according to the second embodiment operates like that of the first embodiment but may be shortened even in the absence of external forces capable of pushing the first stop against the first bracket 14, 15 and may also impose a compressive stress on the organism, which is an advantage over the first embodiment.

Figure 6:
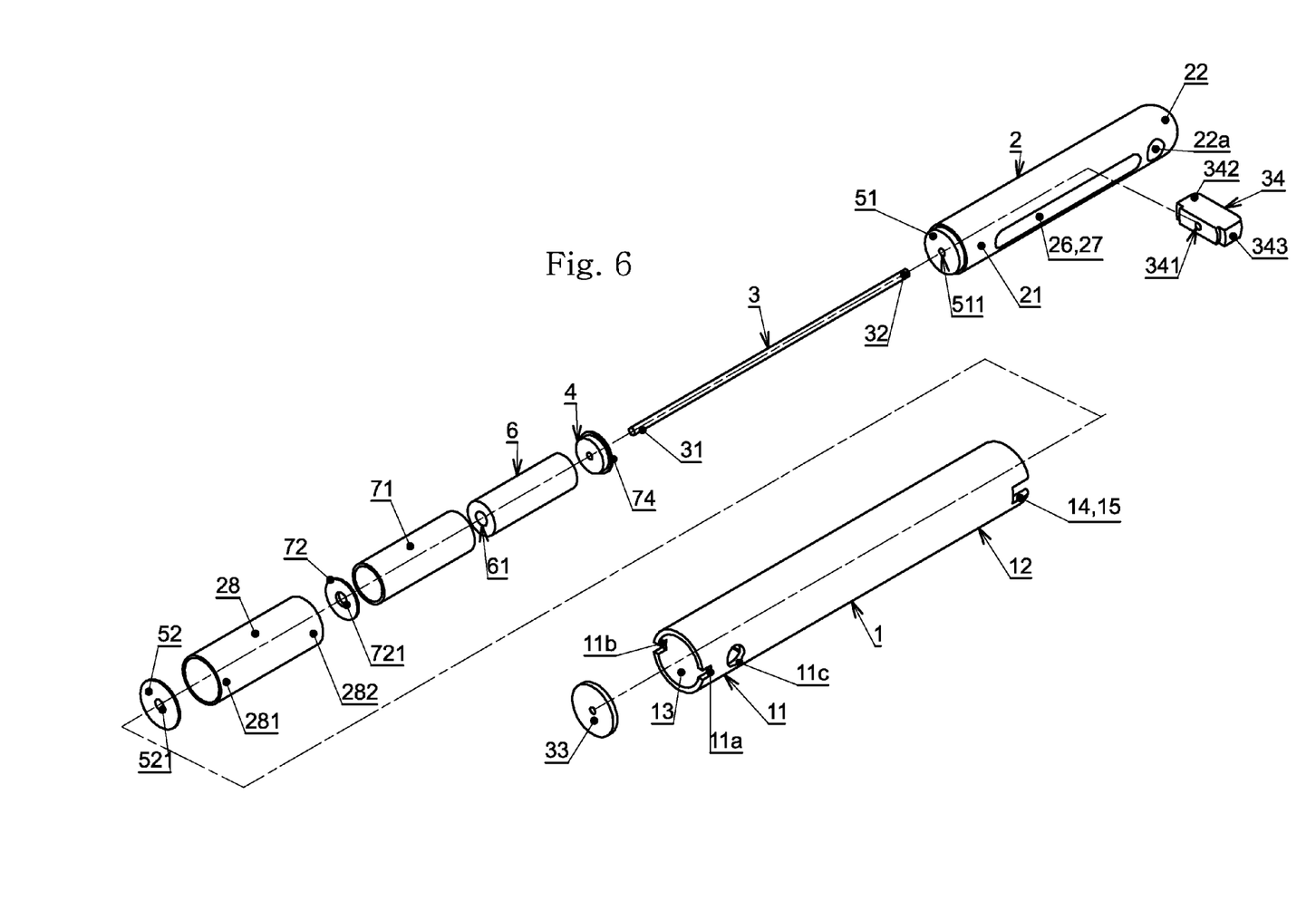
FIG. 6 is an exploded view of a device according to a third embodiment.
Figure 7:
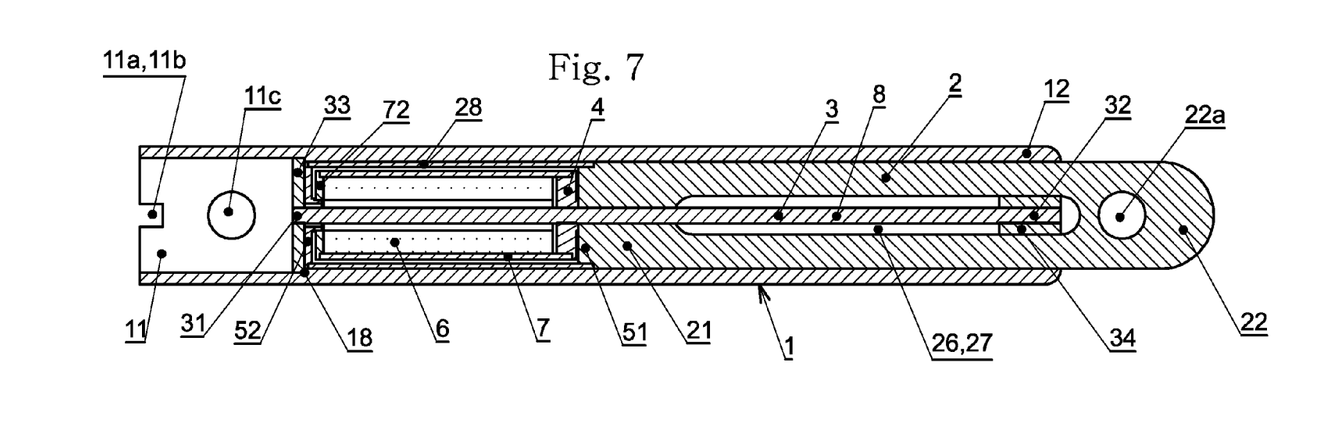
FIG. 7 is a cut view of the device of FIG. 6, assembled and before expansion.
Figure 8:
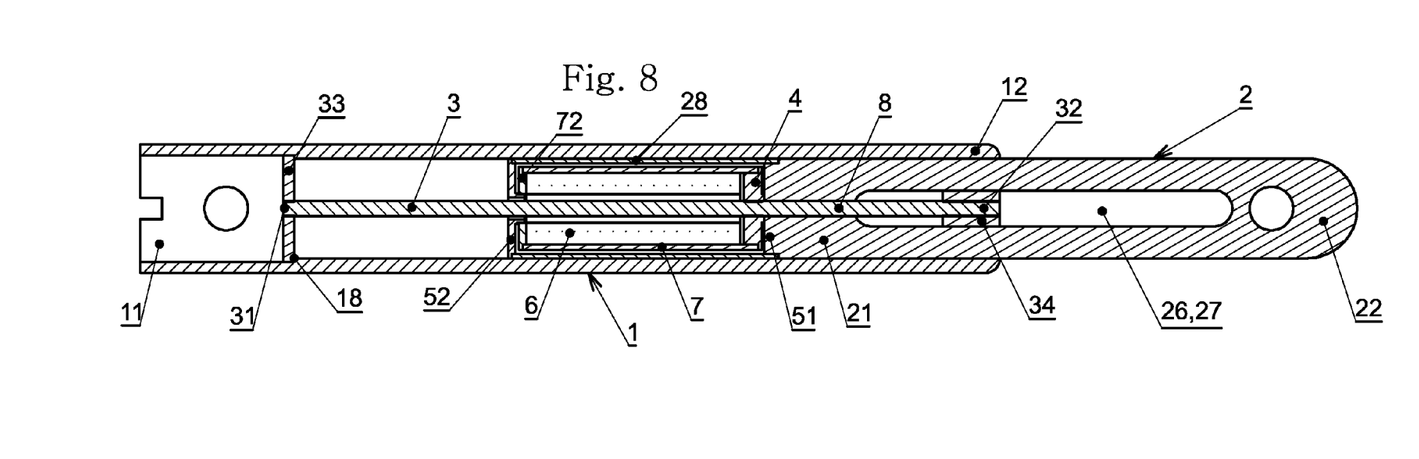
FIG. 8 is a cut view of the device of FIG. 6, assembled and after partial expansion.

Reference is now made to FIGS. 6-8, which illustrate a third embodiment.

The device illustrated on FIGS. 6-8 includes a tubular index part 1 substantially cylindrical and tubular, having a first end 11 and a second end 12.

The first end 11 of the index part 1 includes an attachment structure for attaching ancillary equipment, used for handling the nail during its implantation and explantation. In the illustrated embodiment, the attachment structure includes two recesses 11a, 11b facing each other, and a thread within the tubular part forming the index part 1. The first end 11 of the reference part 1 also includes an attachment structure for attaching to the organism. In the depicted embodiment, this attachment structure includes a hole 11c for the passage of a fixation screw, which may be smooth or threaded.

The second end 12 of the index part 1 includes two recesses 14, 15, which are the so-called first bracket, and a face of which is substantially perpendicular and two faces of which are substantially parallel to the elongation axis of the index part 1.

As in FIGS. 1-5, the device depicted in FIGS. 6-8 includes a transport part 2, a threaded rod 3, an arm 34 also called first stop, a nut 4, a magnet, a cover 71, 51 and a second bearing washer 52.

The transport part 2 includes a first cylindrical end 21 dimensioned to be capable of sliding within the cylindrical housing 13 of the index part 1. The transport part 2 includes two longitudinal elongated throats 26, 27 positioned in such a way that the recesses 14, 15 of the second end 12 of the index part 1 always face each other when the transport part 2 is assembled, however much the device is expanded. The second end 22 of the transport part 2 is provided with attachment structure(s) for attaching to the organism and may have a diameter equal to or greater than that of the first end 21. In the depicted embodiment, the attachment structure includes hole 22a, which may be smooth or threaded, for the passage of a fixation screw.

The arm 34, also called first stop, includes two radial ends 342, 343 capable of cooperating with the recesses 14, 15 of the second end 12 of the reference part 1. The arm 34 includes substantially in its center a preferably threaded housing 341 capable of receiving the second end 32 of the threaded rod 3.

The nut 4 is provided with an inner thread capable of cooperating with the threaded rod 3.

The first bearing washer 51 is machined within the transport part 2 and is provided in its center with a hole 511 the diameter of which is slightly smaller than that of the threaded rod 3.

The magnet 6, preferably in neodymium, iron and boron, resistant to the sterilization temperature, is substantially cylindrical and has, along its axis, a hole 61 in which is inserted the threaded rod 3. The magnet is received within a cavity formed by the cover 71, a washer 72 and the nut 4. The cover 71 is in the shape of a portion of a tube and is closed, at one end, by the washer 72 and at its opposite end by the nut 4. The washer 72 is provided with a hole 721 for the passage of the threaded rod 3 and forms a bearing for the rotation of the magnet.

The device according to the third embodiment depicted in FIGS. 6-8 may be assembled in the following way.

The nut 4 and the cover 71 are assembled and welded together at the junction between the shoulder 74 of the nut 4 and the corresponding opening 711 of the cover. The housing thus created is glued e.g. by way of a silicone glue well tolerated by the organism and the magnet 6 is introduced therein with pressure, so as spread the glue all around. During this phase a removable core protects the hole 61 of the magnet 6 from the glue. The washer 72 and the cover 71 are assembled and welded together at the junction between an annular shoulder of the washer 72 and the annular rim of the tubular cover 71.

The first stop 34 is introduced into the transport part 2 across the longitudinal elongated throats 26, 27. The threaded rod 3 is introduced in the transport part 2, across the hole 511 of the first bearing washer 51, and placed or screwed into the housing 341 of the first stop 34 and then laser welded at an end onto the first stop 34, across one of the longitudinal elongated throats 26, 27.

The assembly formed by the nut 4, the cover 71, the washer 72 and the magnet 6 is assembled with the threaded rod 3 by screwing the nut 4 onto the threaded rod 3.

A tubular element 28 is assembled and welded at its first end 281 to the second bearing washer 52 to form a skirt. This skirt receives the driving shaft formed by the magnet 6 and its cavity 71, 72, 4. At its second end 282, this skirt is assembled and welded to the first end 21 of the transport part 2 onto the bearing washer 51. The threaded rod 3 protrudes across the hole 521 of the second bearing washer 52.

The assembly thus formed is introduced into the second end 12 of the index part, the first stop 34 being received within the recesses 14, 15 of the index part. The index part 1 is provided with a counterbore 13 the bottom of which forms a second bracket capable of receiving the second stop 33. The first end 31 of the threaded rod 3 is welded to this second stop 33.

The device according to the third embodiment disclosed on FIGS. 6-8 may be expanded in the following manner. The second end 22 of the transport part 2 and the first end 11 of the index part 1 being fixed, e.g. by way of bone fixation screws across holes 11c, 22a, a rotating magnetic field is created by an external field source.

The magnetic field source is preferably a permanent magnet hand-operated and which one rotates around the device maintaining one of its poles, i.e. the north pole, constantly turned towards the magnet 6. In an alternate embodiment, the magnet 6 is half-turned around the device with the north pole facing the magnet 6, then half-turned again around the device with the south pole facing the magnet 6, both half-turns being initiated and achieved at the same places.

The pitch of the threaded rod 3 is, for example, between 0.1 and 0.2 mm, so that 5 to 10 revolutions or 10 to 20 half-turns will induce a 1 mm expansion.

In other embodiments, the external magnetic field is provided by electromagnetic devices.

Rotation of the magnet 6 in a first direction rotates the nut 4 on the threaded rod 3, i.e. displacement of the nut 4 towards the first stop 34, thereby displacing the transport part 2 with respect to the index part 1 and expanding the device. The threaded rod 3 works in tension and its loaded length 8 decreases as the nut 4 moves closer to the first end 34 and as the devices expands.

Rotation of the magnet 6 in the second direction causes the shortening of the device when external forces are applied, such as tension of soft tissues and the patient's weight. In each of the three embodiments, the device includes an index part 1, a transport part 2, a threaded rod 3, a nut 4 mounted on the threaded rod 3, a drive shaft including a permanent magnet 6, and drive connector 71, 72, 73 that links the drive shaft to the nut 4. The nut 4 is free to rotate with respect to the index part 1, and the nut 4 moves along the threaded rod 3, the transport part 2 is slidable with respect to the index part 1. The rotation of the threaded rod 3 with respect to the index part 1 is prevented by the first stop 34 cooperating with a first bracket 14, 15, the first stop 34 being fixed to an end 32 of the threaded rod 3, the first bracket 14, being fixed to an end 32 of the threaded rod 3, the first bracket 14, 15 being fixed to an end 12 of the index part 1, the first stop 34 and the nut 4 being located at both sides of the first bracket 14, 15. The longitudinal translation of the threaded rod 3 with respect to the index part 1 in the direction of the first stop 34 towards the first bracket 14 is limited by cooperation of the first stop 34 with the first bracket 14.

The structure that prevents translation of the rod with respect to the index part also prevents rotation of the threaded rod with respect to the index part.

The threaded rod is prevented from rotating with respect to the index part by the structure which limits rotation of the transport part with respect to the index part.

Although the presently disclosed devices keep the advantages of the earlier devices designed by the inventor, in which the threaded rod only works in tension and in which the loaded length of the threaded rod decreases as the device expands, it is clearly different therefrom. For example, in the device disclosed in document FR 2 901 991 in the name of the inventor, the threaded rod is rotated in the first part and no mechanism is provided to prevent its rotation with respect to the first part or the second part: the part referenced 55 in that prior document, called supporting strip, defines a hole in which the threaded rod rotates freely.

In the device disclosed in document WO 2001/78614, the rotation of the magnet rotates the threaded rod, thereby expanding the device.

As a guide, in a presently disclosed device, the diameter of the threaded rod may be about 1.2 to 3 mm, the outer diameter of the magnet may be between 4 and 12 mm, and the length of the permanent magnet may be between 10 and 100 mm.

While FIGS. 1-5 represent a prosthesis for the distal femur (which is the most frequent localization in the clinical practice), any other long bone expandable prosthesis is achievable in the same way, simply by adapting the diameters and lengths of the device's mechanism, and also the geometry of the parts which are in contact with the organism at the provided localization. For example, in order to create a proximal femur prosthesis, the index part will end by a hip joint, the transport part being not substantially modified with respect to a distal femur; for a whole femur the transport part will end by a hip joint, the index part being unchanged with respect to the distal femur. In the same manner one may create prosthetic proximal tibia and humerus prostheses; all long bone expandable prostheses, including the smallest ones, such as radius or elbow, or even a phalanx, may be created according to the present disclosure.

Nails, placed in the medullary cavity of a long bone, or plates, placed along a bone, for maxillofacial or pelvis surgery, for expansion or bone transport may also be made according to the present disclosure, adapting lengths and diameters of the mechanism to the localization of the device, the outer shape of the transport part and the index part, which become substantially cylindrical in the case of a nail, as depicted in FIGS. 6-8, with a bent extremity in the case of a tibial nail for example, and more flattened in the case of a plate and are provided, in a known manner, at their free end, and laterally in the case of plates, with holes capable of receiving bone screws.

The presently disclosed devices may also be employed as equipment for correcting the spine and thorax, such as distraction or compression rods which may be fixed to the pelvis, vertebrae or ribs, adapting lengths and diameters of the mechanism, the ends of the transport part and of the index part becoming substantially cylindrical, as depicted in FIGS. 6-8, and of a diameter compatible with screws or hooks which are used to link them to the skeleton.

Three preferred embodiments of the device have been described in detail, but other embodiments exist which are within the scope of the present disclosure.

Among them, those in which converters for transforming the displacement in a first direction of the nut along the threaded rod into displacement of the transport part with respect to the index part may include a mechanism for amplifying force or displacement, such as a lever. The rotation axis of the lever is for example fixed to the index part, a first end of the lever bears on the nut and a second end on the transport part. The length of the first end/axis and axis/second end of the lever ratio, determines the type of amplification produced.

Other embodiments exist in which the drive connector which links the driving shaft to the bolt includes e.g. a hollow shaft planet reducer, which permits amplification of the force produced by the device.

The drive shaft may in addition include an electrical motor or a spring motor, for example.

The presently disclosed devices are preferably made in materials which are mechanically resistant and well tolerated by the organism, such as stainless steel as e.g. 316L, titanium alloys, polymers such as Poly-ether-ether-ketone (PEEK) or preferably high performance chromium and cobalt alloys such as the austenitic alloy marketed by Arcelor Mittal under the trademark PHYNOX (see AFNOR K 13C20N16Fe15D07).

In addition, the surfaces of the device which undergo friction, in particular the threaded rod 3, may advantageously receive a wear resistant surface treatment, or a surface treatment reducing the friction index, based on diamond like carbon or tungsten disulfide for example.

The presently disclosed devices are particularly useful for creating rods for spinal or thorax correction, bone expansion or transport nails and plates, including for maxillofacial surgery, and expandable prosthesis.

The presently disclosed devices are also suitable for expansion or distortion of soft tissues such as a part of the intestine, or for the artery cerclage, valvuloplasty rings with evolutive geometry, and gastric bands.

I claim:

1. A device for displacing tissues inside an organism, comprising an index part, a transport part, a threaded rod, a nut mounted on the threaded rod, a drive shaft, and a drive connector that links the drive shaft to the nut, the transport part being slidably mounted with respect to the index part and limited in rotation with respect to the index part by a first stop which cooperates with a first bracket of the index part, wherein the rotation of the threaded rod with respect to the index part is prevented by the first stop, the nut being free to rotate with respect to the index part, the nut being movable in translation along the threaded rod, and the nut being movable in translation with respect to the index part.

2. The device of claim 1, wherein the first stop is fixed to a second end of the threaded rod, the first bracket is fixed to a second end of the index part, the first stop and the nut are located on both sides of the first bracket and longitudinal translation of the threaded rod with respect to the index part in the direction of the first stop towards the first bracket is limited by the cooperation of the first stop with the first bracket.

3. The device of claim 1, wherein the drive shaft comprises a permanent magnet.

4. The device of claim 3, wherein the permanent magnet is fixed to the nut.

5. The device of claim 3, wherein a magnetization direction of the permanent magnet is substantially diametral with respect to the axis of the nut.

6. The device of claim 5, wherein said permanent magnet is a neodymium magnet, which comprises an axial hole allowing passage of a threaded bore and wherein the drive connector which links the drive shaft to the nut comprises a rigid envelope fixed to the nut and in which the permanent magnet is maintained.

7. The device of claim 1, further comprising a first converter for transforming the displacement in a first direction of the nut along the threaded rod into a displacement of the transport part with respect to the index part, the first converter comprising a first bracket surface fixed to the nut and a second bracket surface fixed to the transport part, capable of cooperating and substantially perpendicular to the axis of the threaded rod.

8. The device of claim 7, further comprising a second converter for transforming the displacement in a second direction of the nut along the threaded rod in displacement of the transport part with respect to the index part, the second converter comprising a third bracket surface fixed to the nut and a fourth bracket surface fixed to the transport part, capable of cooperating and substantially perpendicular to the axis of the threaded rod.

9. The device of claim 1, further comprising a second converter for transforming the displacement in a second direction of the nut along the threaded rod in displacement of the transport part with respect to the index part, the second converter comprising a third bracket surface fixed to the nut and a fourth bracket surface fixed to the transport part, capable of cooperating and substantially perpendicular to the axis of the threaded rod.

10. The device of claim 1, wherein the index part comprises a prosthetic knee, ankle, shoulder or elbow joint.

11. The device of claim 1, wherein the nut and threaded rod are disposed within the index part.

12. The device of claim 1, wherein the threaded rod is under tension when the device is under load.

13. The device of claim 1, wherein a loaded length of the threaded rod decreases as the device is elongated.

14. The device of claim 1, wherein the index part and the transport part are each longitudinally oriented along an elongation axis, and sliding of the transport part with respect to the index part expands or shortens the device along the elongation axis.

* * * * *